United States Patent
Leemhuis et al.

(10) Patent No.: US 6,177,420 B1
(45) Date of Patent: Jan. 23, 2001

(54) 20-ARALKYL-5α-PREGNANE DERIVATIVES

(75) Inventors: Johannes Antonius Joseph Leemhuis, Mekelenkamplaan; Jaap van der Louw, Pauwoog; Marinus Bernard Groen, Krijtweg, all of (NL)

(73) Assignee: Akzo Nobel N.V., Arnhem (NL)

( * ) Notice: Under 35 U.S.C. 154(b), the term of this patent shall be extended for 0 days.

(21) Appl. No.: 09/423,743

(22) PCT Filed: May 11, 1998

(86) PCT No.: PCT/EP98/02989

§ 371 Date: Nov. 12, 1999

§ 102(e) Date: Nov. 12, 1999

(87) PCT Pub. No.: WO98/52965

PCT Pub. Date: Nov. 26, 1998

(30) Foreign Application Priority Data

May 16, 1997 (EP) .................................................. 97201474

(51) Int. Cl.[7] .......................... A61K 31/575; C07J 9/00; C07J 51/00; C07J 31/00; C07J 41/00
(52) U.S. Cl. ...................... 514/183; 514/183; 514/169; 552/544; 552/546; 552/557; 552/548; 552/520; 552/553; 552/555; 552/519; 552/552
(58) Field of Search .................. 552/544, 520, 552/546, 548, 557, 555, 552, 553; 514/183

(56) References Cited

U.S. PATENT DOCUMENTS 5,716,777 * 2/1998 Byskov et al. .................. 435/2

FOREIGN PATENT DOCUMENTS

| WO 96 00235 | 1/1996 | (WO) . |
| WO 96 27658 | 9/1996 | (WO) . |
| WO 97 00884 | 1/1997 | (WO) . |

OTHER PUBLICATIONS

Barlett et al. (CA 112:158669, abstract of J. Org. Chem. (1990), 55(7), 2215–24.*
Audolin, Max et al. (Tetrahederon, 39 (17), 2799–2802, 1983).*
Byskov et al., *Nature*, 374(6522):559–562 (1995).
Itoh et al., *J. Amer. Oil Chemist' Soc.*, 50:300–303 (1973).

* cited by examiner

Primary Examiner—Sabiha N. Qazi
Assistant Examiner—Sabiha Qazi
(74) Attorney, Agent, or Firm—Mary E. Gormley

(57) ABSTRACT

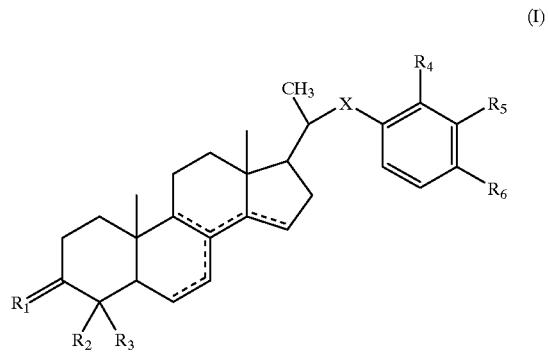

The invention relates to 20-aralkyl-5α-pregnane derivative having general formula (I), or a pharmaceutically acceptable salt thereof, wherein $R_1$ is (H,OR), (H,OSO$_3$H) or NOR; R is H, ($C_{1-6}$)alkyl or ($C_{1-6}$)acyl; each of $R_2$ and $R_3$ is independently hydrogen or ($C_{1-6}$)alkyl; X is a straight chain divalent $C_{1-8}$ hydrocarbon radical, optionally comprising a double or a triple bond; or X is —(CH$_2$)$_m$—CR$_7$R$_8$—; m=0–4; at least one of $R_7$ and $R_8$ is ($C_{1-4}$)alkyl, hydroxy, ($C_{1-4}$)alkoxy or halogen; the other, if present, being hydrogen; or $R_7$ and $R_8$ together represent O or NOR'; R' is H, ($C_{1-6}$)alkyl or ($C_{1-6}$)acyl; each of $R_4$, $R_5$ and $R_6$ is independently hydrogen, hydroxy, ($C_{1-4}$)alkoxy, halogen, NR$_9$, R$_{10}$ or ($C_{1-4}$)alkyl, optionally substituted by hydroxy, alkoxy, halogen or oxo; each of $R_9$ and $R_{10}$ is independently hydrogen or ($C_{1-4}$)alkyl; and the dotted lines indicate a $\Delta^7$ or a $\Delta^8$ double bond, or a pair of conjugated double bonds selected from $\Delta^{7,14}$, $\Delta^{8,14}$ and $\Delta^{6,8(14)}$. The compounds of the invention have meiosis activating activity and can be used for the control of fertility.

8 Claims, No Drawings

20-ARALKYL-5α-PREGNANE DERIVATIVES

This application is a 371 of PCT/EP98/02989 filed on May 11, 1998.

FIELD OF THE INVENTION

The invention relates to 20-aralkyl-5α-pregnane derivatives, to pharmaceutical compositions containing the same, as well as to the use of these 20-aralkyl-5α-pregnane derivatives for the preparation of a medicament for the control of fertility.

BACKGROUND OF THE INVENTION

Sexual reproduction involves a cyclic alternation of diploid and haploid states: diploid cells divide by the process of meiosis to form haploid cells, and the haploid cells fuse in pairs at fertilization to form new diploid cells. The process of meiosis is characterized by two meiotic divisions (I and II), unique to both male and female germ cells. During the process two cell divisions, following one round of DNA replication, give rise to four haploid cells from one single diploid cell. Chromosomal crossover events, during which paternal and maternal genetic material is exchanged, occur during the prophase of the first meiotic division. At the end of the first meiotic division one member of each chromosome pair, composed of two sister chromatids is distributed to each daughter cell. The second meiotic division segregates each sister chromatide into a separate haploid cell. Male and female germ cells are subject to similar meiotic divisions but differ in the regulation of these processes.

In the male meiosis is a continuous process in germ cells derived from a population of immature germ cells, the stem cell spermatogonia. After sexual maturation of the male, spermatogonia from this stem cell population embark on meiosis. The first and second meiotic division proceed without interruption and eventually give rise to four mature spermatozoa.

In the female, primary oocytes start the first meiotic division already during the embryonic stage but they remain arrested in the prophase (dictyate stage) until the female becomes sexually mature. Meiosis resumes at the time of ovulation (egg maturation) after which the first meiotic division is completed and the second meiotic division is initiated. In most vertebrates the second meiotic division is arrested at the metaphase and only completed after fertilization. At the end of the first and of the second meiotic division the cytoplasm divides asymmetrically to produce two secondary oocytes, each with a haploid number of single chromosomes, but greatly differing in size: one is a small polar body, which eventually degenerates, and the other is a large cell containing all the developmental potential. Finally one mature ovum is produced.

The stage at which the developing oocyte is released from the ovary and is ready for fertilization differs in different species. In both invertebrates and vertebrates ovarian accessory cells respond to polypeptides (gonadotropins) produced elsewhere in the body so as to control the maturation of the oocyte and eventually (in most species) ovulation.

In humans the primary oocytes of the newborn female are arrested in prophase of meiotic division I and most are surrounded by a single layer of follicle cells; such an oocyte with its surrounding cells constitute the primordial follicle. A small portion of primordial follicles sequentially begin to grow to become developing follicles: the follicle cells enlarge and proliferate to form a multilayered envelope around the primary oocyte; the oocyte itself enlarges and develops the zona pellucida, an extracellular matrix consisting largely of glycoproteins, and cortical granules, specialized secretory vesicles just under the plasma membrane in the outer region, the cortex of the egg cytoplasm [when the egg is activated by a sperm, these cortical granules release their contents by exocytosis; the contents of the granules act to alter the egg coat so as to prevent other sperms from fusing with the egg].

The developing follicles grow continuously and some of them develop a fluid-filled cavity, or antrum, to become antral follicles. Development of such follicles is dependent on gonadotropins (mainly follicle stimulating hormone-FSH) secreted by the pituitary gland and on estrogens secreted by the follicle cells themselves. Starting at puberty, a surge of secretion by the pituitary of another gonadotropin, luteinizing hormone (LH), activates a single antral follicle to complete its development: the enclosed primary oocyte matures to complete the meiotic division I as the stimulated follicle rapidly enlarges and ruptures at the surface of the ovary, releasing the secondary oocyte within. As is the case with most mammals, the secondary oocyte is triggered to undergo division II of meiosis only if it is fertilized by a sperm.

Studies on the mechanisms controlling initiation and regulation of the meiotic process in male and female germ cells suggest a role for cyclic nucleotides in mediating meiotic arrest. Spontaneous maturation of oocytes can be prevented by compounds that maintain elevated cAMP levels [Eppig, J. and Downs, S. (1984) Biol. Reprod. 30: 1–11]. Purines, like adenosine or hypoxanthine, are thought to be involved in the cAMP mediated maintenance of meiotic arrest [Eppig, J., Ward-Bailey, P. and Coleman, D. (1985) Biol. Reprod. 33: 1041–1049].

The presence of a meiosis regulating substance in a culture system of fetal mouse gonads was first described by Byskov, A. et al. [(1976) Dev. Biol. 52: 193–200]. It was suggested that the concentrations of a meiosis activating substance (MAS) and a meiosis preventing substance (MPS) regulate the meiotic process in concert [Byskov, A. et al. (1994). In "The physiology of reproduction", Eds. Knobil, E. and Neill, J., Raven Press, New York].

More recently (3β,5α,20R)-4,4-dimethylcholesta-8,14,24-trien-3-ol (FF-MAS), isolated from human follicular fluid, and (3β,5α,20R)-4,4-dimethylcholesta-8,24-dien-3-ol, isolated from bull testes, were identified by Byskov, A. et al. [(1995) Nature 374: 559–562] as endogenous meiosis activating substances in human and bovine, respectively. These sterols proved to be able to activate the resumption of meiosis in cultured cumulus enclosed and naked mouse oocytes. Derivatives of the endogenous sterols, having either a saturated or an unsaturated cholestane side chain, have been disclosed in the international patent applications WO 96/00235, WO97/00883 and WO97/00884 (NOVO NORDISK A/S) as meiosis regulating substances.

A drawback of these cholestanes is that they are prone to rapid deactivation in the body [Hall, P. F. (1985) Vitamins and Hormones 42: 315], thereby restricting their therapeutic potential as fertility control agents.

A need therefore exists for regulators of the meiotic process having improved in vivo activity.

SUMMARY OF THE INVENTION

To this end the invention resides in 20-aralkyl-5α-pregnane derivatives having the general formula I, or pharmaceutically acceptable salts thereof,

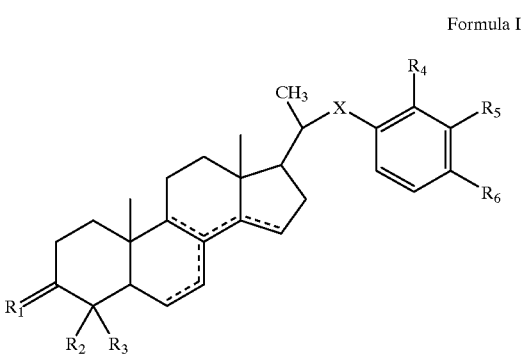

Formula I wherein
- $R_1$ is (H,OR), (H,OSO$_3$H) or NOR;
- R is H, $(C_{1-6})$alkyl or $(C_{1-6})$acyl;
- each of $R_2$ and $R_3$ is independently hydrogen or $(C_{1-6})$ alkyl;
- X is a straight chain divalent $C_{1-8}$ hydrocarbon radical, optionally comprising a double or a triple bond; or X is —(CH$_2$)$_m$—CR$_7$R$_8$—;
- m=0–4;
- at least one of $R_7$ and $R_8$ is $(C_{1-4})$alkyl, hydroxy, $(C_{1-4})$ alkoxy or halogen; the other, if present, is hydrogen; or
- $R_7$ and $R_8$ together represent O or NOR';
- R' is H, $(C_{1-6})$alkyl or $(C_{1-6})$acyl;
- each of $R_4$, $R_5$ and $R_6$ is independently hydrogen, hydroxy, $(C_{1-4})$alkoxy, halogen, NR$_9$,R$_{10}$ or $(C_{1-4})$alkyl, optionally substituted by hydroxy, alkoxy, halogen or oxo;
- each of $R_9$ and $R_{10}$ is independently hydrogen or $(C_{1-4})$ alkyl; and
- the dotted lines indicate a $\Delta^7$ or a $\Delta^8$ double bond, or a pair of conjugated double bonds selected from $\Delta^{7,14}$, $\Delta^{8,14}$ and $\Delta^{6,8(14)}$;
- provided that (3β,4α,24E)-25-(4-hydroxyphenyl)-4-methyl-26,27-dinorcholesta-7,24-dien-3-ol (gramisterol) is excluded.

The disclaimer relates to the disclosure by Hiroitho et al [J. Am. Oil. Chem. Soc. 50, 300–302 (1973)] of the 20-aralkyl-5α-pregnane derivative having formula I wherein $R_1$ is (H,OH); $R_2$ is H and $R_3$ is CH$_3$, or $R_2$ is CH$_3$ and $R_3$ is H; X is —(CH$_2$)$_2$—CH=CH—; $R_4$ and $R_5$ are H; $R_6$ is OH, and wherein the doffed line represents a $\Delta^7$ double bond, i.e. (3β,4α,24E)-25-(4-hydroxyphenyl)-4-methyl-26, 27-dinorcholesta-7,24-dien-3-ol (gramisterol), as a 4-methylsterol component of vegetable oils of wheat germ and other plant tissues.

It has been found that the 20-aralkyl-5α-pregnane derivatives having the general formula I show improved meiosis activating activity.

The invention further resides in a pharmaceutical composition comprising a 20-aralkyl-5α-pregnane derivatives having the general formula I. Pharmaceutical compositions which comprise (3β,4α,24E)-25-(4-hydroxyphenyl)-4-methyl-26,27-dinorcholesta-7,24-dien-3-ol (gramisterol) are within the ambit of the present invention. A further aspect of the invention resides in the use of a 20-aralkyl-5α-pregnane derivative having the general formula I for the manufacture of a medicament for the control of fertility.

DETAILED DESCRIPTION OF THE INVENTION

The term $(C_{1-6})$alkyl as used in the definition of formula I means a branched or unbranched alkyl group having 1–6 carbon atoms, like hexyl, pentyl, butyl, isobutyl, tertiary butyl, propyl, isopropyl, ethyl and methyl. Likewise, the term $(C_{1-4})$alkyl means an alkyl group having 1–4 carbon atoms.

The term $(C_{1-6})$acyl means an acyl group derived from a carboxylic acid having from 1–6 carbon atoms, like hexanoyl, pentanoyl, pivaloyl, butyryl, propanoyl, acetyl and formyl. Also included within the definition of $(C_{1-6})$acyl are acyl groups derived from dicarboxylic acids, like hemi-glutaroyl, hemi-succinoyl, and hemi-maloyl. A preferred $(C_{1-6})$acyl group is hemi-succinoyl.

The term $(C_{1-4})$alkoxy means an alkyloxy having 1–4 carbon atoms, like butyloxy, propyloxy, isopropyloxy, ethyloxy, and, preferably, methyloxy.

The term halogen means F, Cl, Br or I. When halogen is a substituent at an alkyl group, like in the definition of $R_7$ and $R_8$, Cl and F are preferred, F being most preferred.

It is understood that the 20-aralkyl-5α-pregnane derivatives of the invention have the natural configurations 9α, 10β, 13β, 14α, 17β. Preferred compounds according to the invention are the 20-aralkyl-5α-pregnane derivatives of formula I wherein $R_1$ is (H,OR) and the dotted lines indicate the pair of conjugated double bonds selected from $\Delta^{7,14}$, $\Delta^{8,14}$ and $\Delta^{6,8(14)}$. Among these preferred compounds those with the $\Delta^{8,14}$ double bonds are especially preferred. Most preferred are the compounds of the invention wherein the configuration of the 3-OR substituent is the β-configuration.

Highly preferred compounds of the invention are the 20-aralkyl-5α-pregnane derivatives having the general formula I wherein $R_1$ is (H,OR), R is H or $(C_{1-6})$acyl; each of $R_2$ and $R_3$ is independently hydrogen or $(C_{1-6})$alkyl; X is —CH$_2$—; $R_4$, $R_5$ and $R_6$ have the previously given meaning; the dotted lines indicate a pair of conjugated $\Delta^{8,14}$ double bonds; and wherein the configuration of the 3-OR substituent is the β-configuration.

The configuration at position 20 of the 20-aralkyl-5α-pregnane derivatives can be either R or S, preferably R. The compounds of the invention wherein X is a divalent hydrocarbon radical comprising a double bond may have either the E or the Z configuration around the double bond. Both isomers are within the ambit of the present invention.

Particularly preferred compounds according to the invention are:

- (3β,5α,20R)-4,4,20-trimethyl-21-phenylpregna-8,14-dien-3-ol,
- (3β,5α,20R)-4,4,20-trimethyl-21-[4-(trifluoromethyl) phenyl]pregna-8,14-dien-3-ol,
- (3β,5α,20R)-4,4,20-trimethyl-21-phenylpregna-6,8(14)-dien-3-ol,
- (3β,5α,20S)-4,4-dimethyl-23-phenyl-24-norchola-8,14-dien-22-yn-3-ol,
- (3β,5α,20R)-4,4-dimethyl-24-(4-methylphenyl)chola-8,14-dien-23-yn-3-ol,
- (3β,5α,20R)-4,4,20-trimethyl-21-[4-(trifluoromethyl) phenyl]pregna-8,14-dien-3-ol hydrogen butanedioate.

The meiosis activating activity of the 20-aralkyl-5α-pregnane derivatives of the invention is measured in an in vitro oocyte assay as the ability to overcome the hypoxanthine maintained meiotic arrest in denuded oocytes (DO).

The compounds can be used to stimulate meiosis in both male and female and thus can be used as fertility regulating agents. Fertility regulation, or fertility control, comprises contraception and infertility treatment.

For female contraception a 20-aralkyl-5α-pregnane derivative according to formula I can be used for induction of premature maturation of oocytes which are still inside the ovary, before the naturally occurring gonadotropin surge [reduced fertility by inducing premature maturation of oocytes has been demonstrated in rats by Mattheij, J. et al (1993), *Gynecol. Obstet. Invest*. 36: 129–135]. On in vivo administration the compounds of the invention specifically affects germ cells and therefore have the advantage of maintenance of endogenous hormonal levels and subsequently maintenance of normal cycle length. Such a contraceptive method will not cause unwanted side-effects sometimes associated with steroidal contraception (e.g. thrombosis, mood, unscheduled bleeding, malignant breast disease). In this connection it is important to note that the compounds of the invention do no bind to steroid receptors since no binding was found for progesterone receptor, androgen receptor, estrogen receptor and glucocorticoid receptor. Furthermore, it was found that compounds did not have an effect on steroid synthesis or metabolism in human adrenal cells at a dose level which induces oocyte maturation in vitro.

A further advantage of the 20-aralkyl-5α-pregnane derivatives of the invention is their inability to induce maturation in incompetent oocytes (isolated from pre-antral follicles), which indicates that the compounds will not affect the entire oocyte reserve in the ovaries. Only oocytes from antral follicles (competent oocytes) can be induced to mature by the compounds of the invention.

For treatment of female infertility caused by the absence of mature oocytes the compounds of the invention can be administered in vivo to timely stimulate the maturation of competent oocytes.

For treatment of male infertility caused by a shortage of the number of mature spermatozoa the compounds of the invention can be administered in vivo to stimulate the maturation of spermatogonia.

The compounds of the invention can also be used for suppletion of culture media for in vitro fertilization procedures in order to improve oocyte quality.

The 20-aralkyl-5α-pregnane derivative of this invention have the natural configurations 9α, 10β, 13β, 14α, 17β, and possess also one or more additional chiral carbon atoms. The compounds may therefore be obtained as a pure diastereomer, or as a mixture of diastereomers. Methods for obtaining the pure diastereomers are well known in the art, e.g. crystallization or chromatography.

For therapeutic use, salts of the compounds of formula I are those wherein the counterion is pharmaceutically acceptable. However, salts of acids according to formula I [i.e. compounds wherein $R_1$ is $(H,OSO_3H)$] and acid addition salts of bases according to formula I [i.e. compounds wherein $R_4$, $R_5$ and/or $R_6$ are $NR_9R_{10}$], may also find use, for example, in the preparation or purification of a pharmaceutically acceptable compound. All salts, whether pharmaceutically acceptable or not, are included within the ambit of the present invention.

Examples of salts of acids according to the invention are mineral salts such as sodium salt, potassium salt, and salts derived from organic bases like ammonia, imidazole, ethylenediamine, triethylamine and the like.

Examples of acid addition salts include those derived from mineral acids such as hydrochloric acid, phosphoric acid, sulphuric acid, preferably hydrochloric acid, and organic acids like citric acid, tartaric acid, acetic acid, lactic acid, maleic acid, malonic acid, fumaric acid, glycolic acid, succinic acid, and the like.

The compounds of formula I or a pharmaceutically acceptable salt thereof, also referred to herein as the active ingredient, may be administered enterally or parenterally. The exact dose and regimen of administration of the active ingredient, or a pharmaceutical composition thereof, will necessarily be dependent upon the therapeutic effect to be achieved (treatment of infertility; contraception), and will vary with the particular compound, the route of administration, and the age and condition of the individual subject to whom the medicament is to be administered.

In general parenteral administration requires lower dosages than other methods of administration which are more dependent upon adsorption. However, a dosage for humans preferably contains 0.0001–25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

In case of in vitro or ex vivo applications, like in IVF applications, the compounds of the inventions are to be used in the incubation media in a concentration of approximately 0.01–5 μg/ml.

The present invention thus also relates to pharmaceutical compositions comprising a 20-aralkyl-5α-pregnane derivative according to formula I, i.e. including pharmaceutical compositions comprising (3β,4α,24E)-25-(4-hydroxyphenyl)-4-methyl-26,27-dinorcholesta-7,24-dien-3-ol (gramisterol), in admixture with pharmaceutically acceptable auxiliaries, and optionally other therapeutic agents. The auxilliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration. The compositions may be prepared by any method well known in the art of pharmacy, for example, using methods such as those described in Gennaro et al., Remington's Pharmaceutical Sciences (18th ed., Mack Publishing company, 1990, see especially Part 8: *Pharmaceutical Preparations and Their Manufacture*).

Such methods include the step of bringing in association the active ingredient with any auxilliary agent. The auxilliary agent(s), also named accessory ingredients, include those conventional in the art (Gennaro, supra), such as, fillers, binders, diluents, disintegrants, lubricants, colorants, flavoring agents and wetting agents.

Pharmaceutical compositions suitable for oral administration may be presented as discrete dosage units such as pills, tablets or capsules, or as a powder or granules, or as a solution or suspension. The active ingredient may also be presented as a bolus or paste. The compositions can further be processed into a suppository or enema for rectal administration.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example, water prior to use.

Compositions, or formulations, suitable for administration by nasal inhalation include fine dusts or mists which may be generated by means of metered dose pressurised aerosols, nebulisers or insufflators.

The 20-aralkyl-5α-pregnane derivatives of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303, 306 (AKZO N.V.).

The compounds of the invention may be produced by various methods known in the art of organic chemistry in general, and especially in the art of the chemistry of steroids [see for example: Fried, J. and Edwards, J. A., "Organic Reactions in Steroid Chemistry", Volumes I and II, Van Nostrand Reinhold Company, New York, 1972].

The 20-aralkyl-5α-pregnane derivatives of formula I can generally be prepared from unsaturated 20-methylpregna-3, 21-diol derivatives of formula II,

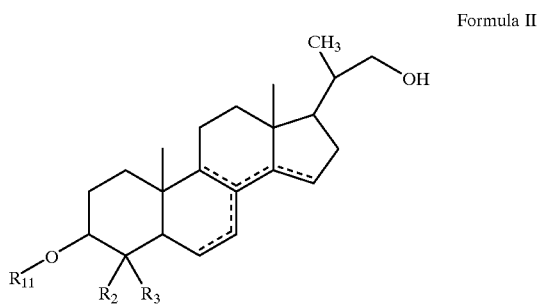

Formula II in which $R_2$ and $R_3$ are independently hydrogen or $(C_{1-6})$ alkyl; $R_{11}$ is an acyl protecting group, such as benzoyl, acetyl, pivaloyl and the like; and wherein the dotted lines represent a $\Delta^7$ or a $\Delta^8$ double bond, or a pair of conjugated double bonds selected from $\Delta^{6,8(14)}$, $\Delta^{7,14}$ and $\Delta^{8,14}$.

Starting material for the preparation of the intermediates of formula II is for example (20S)-3-oxopregn-4-en-20-carboxaldehyde, which aldehyde can be obtained by ozonolysis from stigmasta-4,22-dien-3-one as described by T. Veysoglu et al [Synthesis 807 (1980)] and which is also commercially available (Sigma, USA). The aldehyde is selectively reduced to (20S)-21-hydroxy-20-methylpregn-4-en-3-one [B. M. Trost et al, J. Amer. Chem. Soc. 105, 5075 (1983)], whereupon the resulting hydroxy function is protected as an ether, e.g. the ethoxyethyl ether, the tetrahydropyranyl (THP) ether, or a silylether, such as the triisopylsilyl ether, the t-butyldimethylsilyl ether, or the t-butyldiphenylsilyl ether, and the like.

Suitable protective groups are known in the art, for example from Greene, T. W. and Wuts, P. G. M.: *Protective Groups in Organic Synthesis*, Second Edition, Wiley, N.Y., 1991.

Optionally, the resulting hydroxy protected (20S)-21-hydroxy-20-methylpregn-4-en-3-one can be mono- or dialkylated at C-4, for instance, it can be dimethylated. Alkylation can be performed using standard procedures, such as the potassium tert-butoxide-methyliodide method [R. E. Dolle et al, J. Org. Chem. 51, 4047 (1986)], the use of lithium diisopropylamide (LDA)-methyliodide (MeI), and similar methods known in the art.

Optionally, the $\Delta^4$ compound can be converted to a $\Delta^5$ derivative by reaction with a base followed by quenching with water [J. B. Jones et al, Can. J. Chem. 46, 1459 (1968)].

The carbonyl group at C-3 can subsequently be reduced to hydroxy with the use of reducing agents like for example lithium aluminium hydride, sodium borohydride, or other hydride reducing agents known in the art. The resulting 3-hydroxy compounds can be protected as an ester, e.g. an acetate ester, a benzoate ester, or a pivalate ester, and the like. A $\Delta^5$ system can be converted to a $\Delta^{5,7}$-diene system by the sequence: bromination at C-7 followed by dehydrobromination. The bromination reaction can be carried out thermally [Schroepfer, G. J. Jr., et al, Chem. Phys. Lipids 47, 187 (1988)] or photochemically [Prelle, A. et al, Heterocycles 28, 333 (1989)]. In either case, brominating agents which can be used are N-bromosuccinimide, 1,3-dibromo-5,5-dimethylhydantoin and the like. Dehydrobrominating agents include N,N-diisopropylethylamine, 2,4,6-trimethylpyridine, trimethylphosphite, tetrabutylammonium fluoride, and others.

A $\Delta^{5,7}$ diene system can now be converted to a $\Delta^{6,8(14)}$ diene system, a $\Delta^{7,14}$ diene system, or a $\Delta^{8,14}$ diene system. Methods used are known in the art. For conversion to the $\Delta^{6,8(14)}$ derivative, see e.g. Kaneko, C. et al, Chem. Pharm. Bull. 26, 3582 (1978). For conversion to the $\Delta^{7,14}$ derivative, see e.g. Wilson, W. K. et al, J. Org. Chem. 53, 1713 (1988). For conversion to the $\Delta^{8,14}$ derivative, see e.g. Schroepfer, G. J. Jr., et al, Chem. Phys. Lipids 47, 187 (1988) or Dolle, R. E. et al, J. Org. Chem. 53, 1563 (1988). Conversion of a $\Delta^{5,7}$ diene system to a $\Delta^{6,8(14)}$ diene system, a $\Delta^{7,14}$ diene system, or a $\Delta^{8,14}$ diene system may result in mixtures of these isomers. Methods for obtaining the pure compounds are well known in the art e.g. crystallization or chromatography using a silica column loaded with a silver salt. $\Delta^7$ Compounds are obtained from the $\Delta^{5,7}$ diene system by reduction with lithium in liquid ammonia [Lederer, F. et al, Bull. Soc. Chim. Fr. 1295 (1965)] or by hydrogenation. Hydrogenation catalysts which can be used include Raney nickel [Gautschi, F. et al, J. Biol. Chem. 233, 1343 (1958)], Wilkinson's catalyst [Canonica, L. et al, Steroids 11, 287 (1968)] and others. $\Delta^8$ Derivatives are prepared from $\Delta^{8,14}$ dienes by the sequence: selective hydroboration of the $\Delta^{14}$ double bond followed by deoxygenation of the 15-hydroxy compound produced [Dolle, R. E. et al, J. Amer. Chem. Soc. 111, 278 (1989)]. The preparation of the unsaturated 3-protected 20-methylpregna-3,21-diol derivatives of formula II is completed by deprotection of the 21-hydroxy function.

Manipulation of the $\Delta^{5,7}$ diene system can be accompanied by deprotection of the hydroxy group at C-21. If not, the hydroxy group has yet to be deprotected.

The 21-aryl-20-methylpregn-3-ol derivatives (X=—$CH_2$—) of the invention are obtained by oxidation of the compounds of formula II to the corresponding pregna-20-carboxaldehydes, followed by a condensation reaction of these aldehydes with an unsubstituted or suitably substituted phenylmetal compound, deoxygenation at C-21 of the 3-protected 21-aryl-20-methylpregna-3,21-diol derivatives produced and, finally, deprotection of the hydroxy group at C-3.

The oxidation of the 21-hydroxy group can be carried out by using an Oppenauer oxidation, a Swern oxidation, a Moffatt oxidation, a Dess-Martin oxidation, or by the use of chromium(VI) reagents like Jones reagent, pyridinium dichromate, pyridinium chlorochromate and similar reagents known in the art.

Unsubstituted or substituted phenylmetal compounds which can be used in the condensation reaction with the pregna-20-carboxaldehydes include aryllithium-, arylmagnesium-, arylzinc- or arylcerium compounds.

Replacement of the ensuing 21-hydroxy group by hydrogen (deoxygenation) in the 3-protected 21-aryl-20-methylpregna-3,21-diol derivatives can be carried out by esterification with methyl oxalyl chloride followed by reaction with tributyltin hydride/2,2'-azabis(isobutyronitrile). The deoxygenation might also be accomplished by a Barton deoxygenation reaction or similar techniques known in the art [M. Ramaiah, Tetrahedron 43, 3541 (1987)], or by conversion of the 21-hydroxy group to a leaving group such as a halogen like chlorine, bromine, or iodine, or in particular the tosyloxy group or the mesyloxy group, followed by reduction with a hydride reducing agent, or by the use of Raney nickel, or with e.g triethylsilane in combination with a Lewis acid. Finally, deprotection of the 3-hydroxy function is accomplished using standard methods.

The unsaturated 23-aryl-24-norcholan-3-ol compounds (X=—CH$_2$—CH$_2$—) of the invention can be prepared from the unsaturated 3-protected 20-methylpregna-3,21-diol derivatives of formula II as follows. The hydroxy function at C-21 can be converted to a leaving group, such as a halogen like chlorine, bromine, or iodine, or in particular the tosyloxy group or mesyloxy group, whereupon the products thus obtained can be converted by reaction with potassium cyanide or sodium cyanide to 20-methylpregna-21-carbonitrile derivatives. The latter can be converted to the corresponding 21-carboxaldehydes by treatment with a reducing agent such as diisobutylaluminium hydride or other reducing agents capable of converting a carbonitrile group into a carboxaldehyde group. Since the reduction also leads to deprotection of the hydroxy function at C-3, the 3-hydroxy group is to be reprotected as an ether, e.g. a ethoxyethyl ether or a THP ether, a silylether, e.g. a trimethylsilyl ether, or an acyl protecting group as described above. The final conversion to the 23-aryl-24-norcholan-3-ol compounds of the invention can be carried out by the sequence (vide supra): reaction with an unsubstituted or suitably substituted phenylmetal compound, replacement of the 23-hydroxy group by hydrogen by deoxygenation and, finally, deprotection of the 3-hydroxy group.

The compounds of the invention in which X is a straight chain divalent C$_3$-hydrocarbon radical can be prepared using procedures similar to those described for 23-aryl-24-norcholan-3-ol derivatives described above. First, the compounds of formula II are converted to an aldehyde having the required number of methylene groups in the side chain. Then, addition of an unsubstituted or suitably substituted phenylmetal compound, deoxygenation of the hydroxy compound formed and, finally, deprotection of the 3-hydroxy group is carried out as described above. Techniques for homologation are known in the art, see for example Mathieu, J. et al: Formation of C—C Bonds, Vol. I–III, Georg Thieme Publishers, Stuttgart, 1973.

The compounds of the invention in which X represents —(CH$_2$)$_m$—CR$_7$R$_8$— wherein m=0–4 and wherein R$_7$ is hydroxy and R$_8$ is hydrogen can be prepared in a similar way as described above. In this case, the hydroxy group which is formed by reaction with the arylmetal compound is maintained, i.e. the deoxygenation is left out. The arylcarbinols produced can optionally be converted, using methods well known in the art of general chemistry, to other compounds of formula I, namely the compounds of the invention in which X represents —(CH$_2$)$_m$—CR$_7$R$_8$— wherein m=0–4 and wherein R$_7$ and R$_8$ are independently (C$_{1-4}$)alkyl, (C$_{1-4}$)alkoxy, or halogen, or wherein R$_7$ and R$_8$ together represent O, or NOR', wherein R' is H, (C$_{1-6}$)alkyl, or (C$_{1-6}$)acyl.

The compounds of the invention in which X is a straight chain divalent C$_{1-8}$ hydrocarbon radical can also be prepared from intermediates of formula II by converting the 21-hydroxy group to a leaving group, as already described, followed by a transition metal mediated, e.g. copper(I)-catalyzed, reaction with a suitably substituted phenylmetal compound or suitably substituted ω-phenylalkylmetal compound [Li, Mg, Zn; see Morisaki. M. et al, Chem. Pharm. Bull. 28, 606 (1980); and Lipshutz, B. H. et al in Org. Reactions 41, p. 135, Wiley, N.Y., 1992].

The compounds of the invention in which X is a straight chain divalent C$_1$-hydrocarbon radical containing a double bond can be prepared by Wittig reaction of pregna-20-carboxaldehydes or 20-methylpregna-21-carboxaldehydes, whose synthesis is described above, or of cholan-24-al derivatives, and so on, with unsubstituted or suitably substituted benzyltriphenylphosphonium halides, or unsubstituted or suitably substituted ω-phenylalkyltriphenylphosphonium halides. For methods used for the Wittig olefination reaction, see Maercker, A. in Org. Reactions 14, p. 270, Wiley, N.Y., 1965. Alternatively, Peterson reactions can be used, see Ager, D. J. in Org. Reactions, 38, p. 1, Wiley, N.Y., 1990.

The compounds of the invention in which X is a straight chain divalent C$_{1-8}$ hydrocarbon radical containing a double bond can also be prepared by a metal mediated coupling of 24-norchol-22-enes, chol-23-enes, or 26,27-dinorcholest-24-enes, and so on, substituted at C-23, C-24, C-25, respectively, with halogen (Cl, Br, I) or a triflate group, with an unsubstituted or suitably substituted phenylmetal compound or ω-phenylalkylmetal compound (e.g. Al, Li, Mg, Zn, B, Sn, Cu, Zr). They can also be prepared by a similar reaction of 24-norchol-22-enes, chol-23-enes, or 26,27-dinorcholest-24-enes, and so on, substituted at C-23, C-24, C-25, respectively, with a metal (Al, Li, Mg, Zn, B, Sn, Cu, Zr), with a suitably substituted phenylhalide or ω-phenylalkylhalide (Cl, Br, I), or sulfonate. Methods used are known in the art, see Knight, D. W. in *Comprehensive Organic Synthesis* 3, p. 241 and 481, Pergamon Press, Oxford, 1991; or K. Tamao, ibid. 3, p. 435.

The compounds of the invention in which X is a straight chain divalent C$_{1-8}$ hydrocarbon radical containing a triple bond can be prepared by a transition metal mediated coupling of 24-norchol-22-ynes, chol-23-ynes, or 26,27-dinorcholest-24-ynes with a suitably substituted phenyl halide [Cl, Br, I; see Takahashi, S. et al, Synthesis 627 (1980)]. Other compounds in this class can be prepared by metallation (e.g. Li, Mg, Na, K, Al) of said acetylene derivatives followed by reaction with suitably substituted ω-phenylalkyl halides or sulfonate esters [Garratt, P. J. in Comprehensive Organic Synthesis, 3, p. 271, Pergamon Press, Oxford, 1991]. Alternatively, they can be prepared by reaction of 20-methylpregn-21-ol derivatives, 24-norcholan-23-ol derivatives, or cholan-24-ol derivatives, and so on, in which the hydroxy group is converted to a leaving group (vide supra), with an unsubstituted or suitably substituted ω-phenylalk-1-ynylmetal compound.

Compounds of formula I in which R$_1$ is (H,OH) may serve as starting material for the synthesis, using methods known in the art, of compounds of formula I in which R$_1$ is (H,OR), (H,OSO$_3$H) or NOR, and R is H, (C$_{1-6}$)alkyl, or (C$_{1-6}$)acyl.

The invention is further illustrated by the following examples.

Scheme I

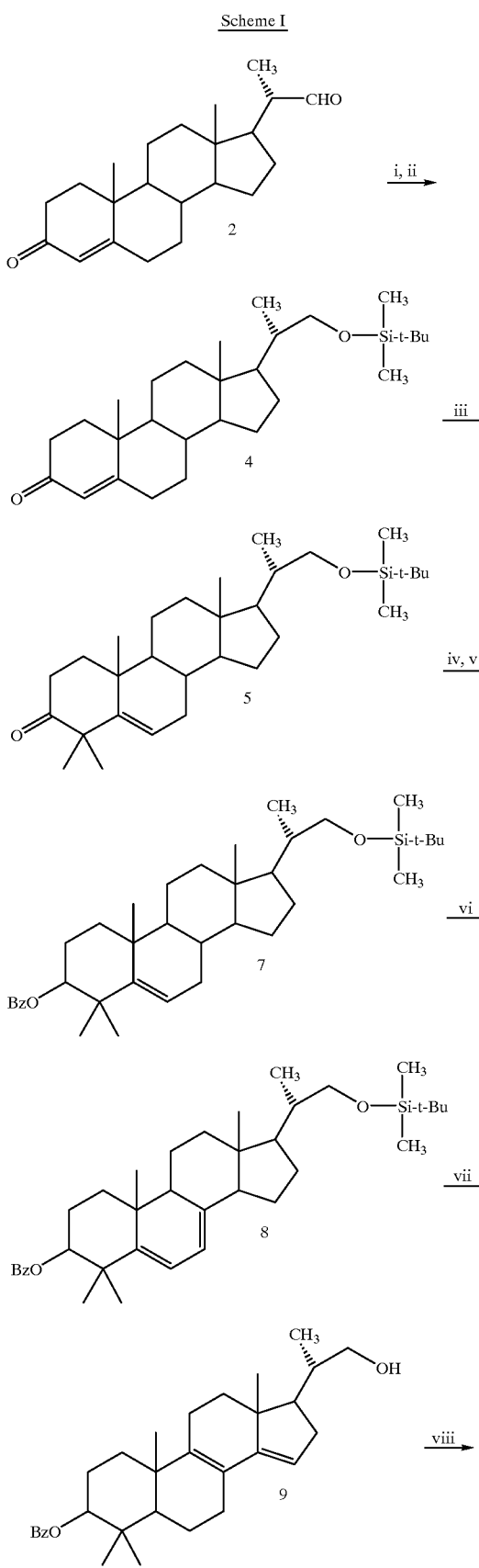

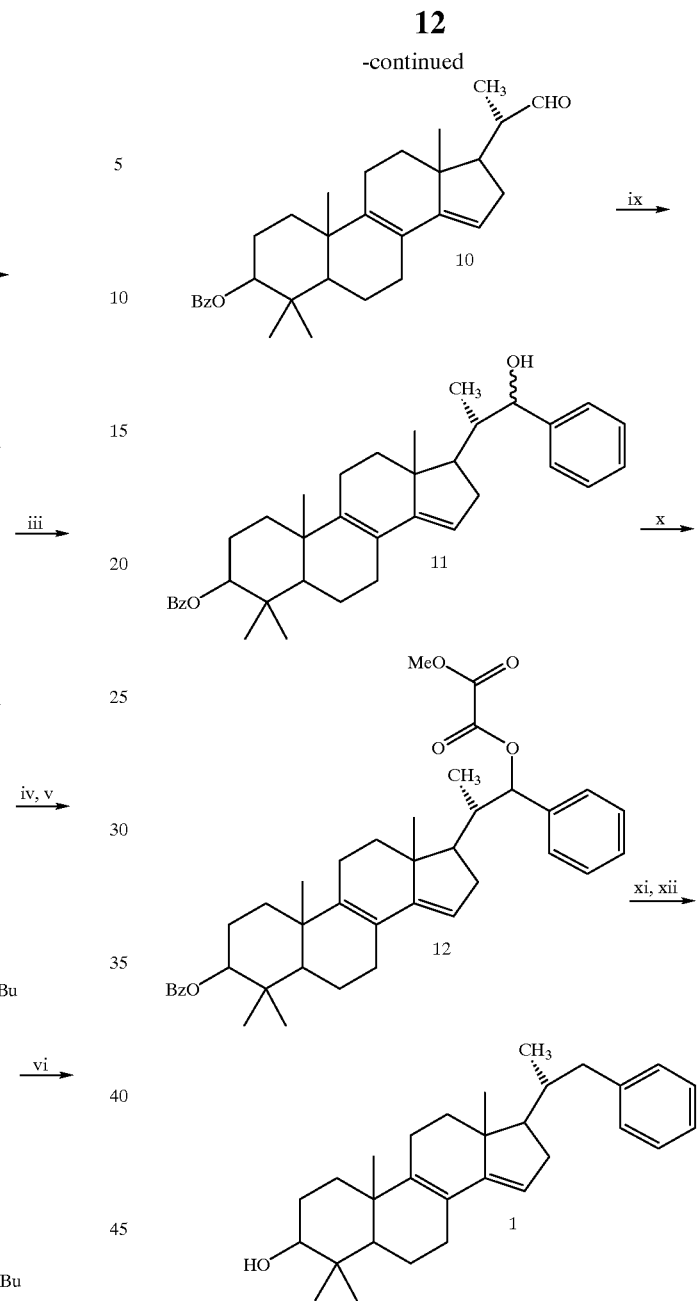

EXAMPLE 1

(3β,5α,20R)-4,4,20-Trimethyl-21-phenylpregna-8,14-dien-3-ol. (1) (Scheme I)

i)—A solution of (20S)-3-oxopregn-4-ene-20-carboxaldehyde (2) (125 g) in dry ethanol (1250 ml) was cooled to −10° C., whereupon a solution of sodium borohydride (4.4 g) in dry ethanol (80 ml) was added in 30 min. After stirring the mixture for 2 h at −10° C., the reaction was quenched by adding a 50% aqueous solution of acetic acid. The reaction mixture was concentrated under reduced pressure to 25% of its original volume and then poured into ice-water (5 l). The resulting suspension was stirred overnight and filtered. The residue was washed with water and dried to give (20S)-21-hydroxy-20-methylpregn-4-en-3-one (3) (124 g) which was used in the following step without further purification.

ii)—A solution of the alcohol 3 (124 g) obtained in the previous step and of imidazole (176 g) in dry N,N-dimethylformamide (1730 ml) was cooled to 10° C. t-Butyldimethylsilyl chloride (112 g) was added in one portion and the mixture was stirred at room temperature for 2 h. Then it was poured into a mixture of ice-water (10 l) and of a saturated aqueous solution of sodium hydrogen carbonate (750 ml). The resulting suspension was filtered and the residue was washed with water. Drying of the residue afforded (20S)-21-[[(1,1-dimethylethyl)dimethylsilyl]oxy]-20-methylpregn-4-en-3-one (4) (169.3 g), which was used in the following step without further purification.

iii)—A mixture of potassium t-butoxide (169.5 g) and dry t-butanol (3750 ml) was warmed to 45° C. A solution of the ketone 4 (169.3 g) in dry tetrahydrofuran (375 ml) was added and the mixture was stirred for 10 min. Iodomethane (187.5 ml) was added in 10 min. and stirrring was continued for 3 h. The reaction mixture was concentrated under reduced pressure to a volume of 1.5 l and then poured into ice-water (10 l). After stirring of the mixture for 2 h the suspension was filtered. The residue was washed with water, dried and purified by crystallization from acetone to give (20S)-21-[[(1,1-dimethylethyl)dimethylsilyl]oxy]-4,4,20-trimethylpregn-5-en-3-one (5) (136.9 g).

iv)—A solution of the ketone 5 (140 g) obtained in the previous step in dry tetra-hydrofuran (1400 ml) was added in 30 min. to an ice-cooled suspension of lithium aluminium hydride (35 g) in tetrahydrofuran (1750 ml). After stirring of the mixture for 1 h at room temperature, the reaction was quenched by addition of a saturated aqueous solution of sodium sulfate (152 ml), followed by water (39 ml). Ethyl acetate (1750 ml) was added, and the mixture was filtered over celite. The filtrate was concentrated under reduced pressure to give (3β,20S)-21-[[(1,1-dimethylethyl) dimethylsilyl]oxy]-4,4,20-trimethylpregn-5-en-3-ol (6) (136.3 g), which was used in the following step without further purification.

v)—A solution of the alcohol 6 (132.5 g) obtained in the previous step in dry pyridine (1310 ml) was cooled to 0° C. Benzoyl chloride (65.7 ml) was added in 5 min. and the reaction mixture was stirred for 1 h at room temperature. Then it was poured into ice-water (6650 ml) and the resulting suspension was stirred over-night. The precipitate was collected by filtration and washed with water (40–50° C.). The residue was dried and purified by crystallization from acetone to give (3β,20S)-21-[[(1,1-dimethylethyl) dimethylsilyl]oxy]-4,4,20-trimethylpregn-5-en-3-ol benzoate (7) (113.6 g).

vi)—A mixture of the benzoate 7 (94.0 g) obtained in the previous step, dry toluene (810 ml), dry cyclohexane (810 ml) and N-bromosuccinimide (36.1 g) was heated under reflux for 10 min. The reaction mixture was cooled, another portion of N-bromosuccinimide (36.1 g) was added, and reflux was continued for another 10 min. The reaction mixture was cooled, a saturated aqueous solution of sodium thiosulfate (1620 ml) was added and the resulting mixture was stirred for 30 min. The organic phase and the aqueous phase were separated and the latter extracted two times with toluene. The combined organic phases were dried over sodium sulfate and concentrated under reduced pressure. A solution of the crude product thus obtained in dry toluene (2835 ml) and N,N-diisopropylethylamine (284 ml) was heated under reflux for 1 h. Then it was cooled and washed with a saturated aqueous solution of sodium hydrogen carbonate, a saturated aqueous solution of ammonium chloride and with brine, the aqueous phase each time being extracted with ethyl acetate. The combined toluene and ethyl acetate solutions were dried over sodium sulfate and concentrated under reduced pressure to give (3β,20S)-21-[[(1,1-dimethylethyl)dimethylsilyl]oxy]-4,4,20-trimethylpregna-5,7-dien-3-ol benzoate (8) (134 g) which was used in the following step without further purification.

vii)—A mixture of compound 8 (32.3 g), toluene (84 ml), ethanol (96%; 588 ml) and concentrated hydrochloric acid (84 ml) was heated under reflux for 3 h. The mixture was cooled and poured into a saturated aqueous solution of sodium hydrogen carbonate (1 l). The product was extracted into ethyl acetate; the combined organic phases were washed with brine, dried over sodium sulfate, and concentrated under reduced pressure. Column chromatography afforded a 3:1 mixture (17.4 g) of (3β,5α,20S)-4,4,20-trimethylpregna-8,14-diene-3,21-diol 3-benzoate (9) and (3β,5α,20S)-4,4,20-trimethylpregna-6,8(14)-diene-3,21-diol 3-benzoate. The mixture was used as such in the next step.

viii)—A solution of dry dimethyl sulfoxide (1.97 ml) in dry dichloromethane (76 ml) was cooled to –78° C., and a solution of oxalyl chloride (1.53 ml) in dry dichloromethane (38 ml) was added in 30 min. Stirring was continued for another 5 min. and a solution of the mixture (5.0 g) obtained under vii in dry tetrahydrofuran (36 ml) was added in 20 min. Stirring at –78° C. was continued for 5 h, after which triethylamine (7.3 ml) was added and the mixture was allowed to rise to room temperature. Water was added and the product was extracted into dichloromethane. The combined organic phases were washed with water, dried over sodium sulfate, and concentrated under reduced pressure to afford (3β,5α,20S)-3-(benzoyloxy)-4,4-dimethylpregna-8,14-diene-20-carboxaldehyde (10) (6.14 g), which was used in the following step without further purification.

ix)—A solution of the aldehyde 10 (2.0 g), obtained in the previous step, in dry tetrahydrofuran (17 ml) was added dropwise to a 1 M solution of phenylmagnesium bromide (13 ml) in tetrahydrofuran. The reaction mixture was stirred at room temperature for 3 h. A saturated aqueous solution of ammonium chloride was added and the product was extracted into ethyl acetate. The combined organic phases were washed with water, dried over sodium sulfate, and concentrated under reduced pressure to give (3β,5α,20S)-4,4,20-trimethyl-21-phenylpregna-8,14-diene-3,21-diol 3-benzoate (11) (3.0 g) which was used in the following step without further purification.

x)—A solution of the alcohol 11 (3.0 g) in dry dichloromethane (26.7 ml) and dry pyridine (5.2 ml) was added dropwise to an ice-cooled solution of methyl oxalyl chloride (1.95 ml) in dry dichloromethane (9.7 ml). The mixture was stirred at room temperature for 1 h. Water was added and the product was extracted into ethyl acetate. The combined organic phases were washed with a 4 M aqueous solution of hydrochloric acid and with water, dried over sodium sulfate, and concentrated under reduced pressure to give (3β,5α,20S)-4,4,20-trimethyl-21-phenylpregna-8,14-diene-3,21-diol 3-benzoate 21-(methyl ethanedioate) (12) (3.58 g), which was used in the following step without further purification.

xi)—A solution of methyl ethanedioate 12, the product obtained in the previous step, in dry toluene (150 ml) was heated at reflux temperature. Tributyltin hydride (2.5 ml) was added followed by 2,2'-azabis(isobutyronitrile) (35 mg). Addition of portions (35 mg) of the latter compound was repeated every 15 min. until the reaction was complete (5 h). The reaction mixture was cooled, water was added, and the product was extracted into dichloromethane. The combined organic phases were washed with water, dried over sodium sulfate, and concentrated under reduced pressure. Column chromatography afforded (3β,5α,20R)-4,4,20-trimethyl-21-phenylpregna-8,14-dien-3-ol benzoate (13) (0.84 g).

xii)—Potassium hydroxide (0.45 g) was added to a solution of compound 13 (0.84 g) in a mixture of tetrahydrofuran (8.4 ml), methanol (8.4 ml) and water (0.45 ml). The mixture was heated under reflux overnight. After cooling, water was added and the resulting precipitate collected by filtration. The residue was washed with water and dried. Column chromatography and crystallization from dichloromethane/acetone afforded (3β,5α,20R)-4,4,20-trimethyl-21-phenylpregna-8,14-dien-3-ol (1) (0.29 g). M.p. 179–186° C. The product contained 30% (w/w) of (3β,5α,20R)-4,4,20-trimethyl-21-phenylpregna-6,8(14)-dien-3-ol.

EXAMPLE 2

Starting from (3β,5α,20S)-3-(benzoyloxy)-4,4-dimethylpregna-8,14-diene-20-carboxaldehyde 10, described under viii of Example 1, and using reaction steps analogous to those described under ix–xii of Example 1, the following compounds were prepared:

A)—(3β,5α,20R)-4,4,20-Trimethyl-21-(3-methylphenyl) pregna-8,14-dien-3-ol. M.p. 140.5–143.5° C.

B)—(3β,5α,20R)-4,4,20-Trimethyl-21-[4-(trifluoromethyl)phenyl]pregna-8,14-dien-3-ol. M.p. 169–171° C.

EXAMPLE 3

(3β,5α,20R)-4,4,20-Trimethyl-21-phenylpregna-6,8 (14)-dien-3-ol i)—Hydrogen chloride gas was passed into a solution of (3β,20S)-21-[[(1,1-dimethylethyl)dimethylsilyl]oxy]-4,4,20-trimethylpregna-5,7-dien-3-ol benzoate (compound 8; Example 1, step vi; 25.0 g) and acetic anhydride (40 ml) in chloroform (250 ml) for 30 min. The mixture was heated at reflux temperature for 50 min.; addition of hydrogen chloride gas was continued for the first 20 min. After cooling to 0° C., an aqueous solution of ammonium hydroxide (5%) was added, and the mixture was stirred for 1.5 h. The product was extracted into dichloromethane; the combined organic phases were washed with a saturated aqueous solution of sodium hydrogencarbonate and brine, dried over sodium sulfate and concentrated under reduced pressure to give (3β,5α,20S)-21-[[( 1,1-dimethylethyl)dimethylsilyl] oxy]-4,4,20-trimethylpregna-6,8(14)-dien-3-ol benzoate (24.6 g). The product was used as such in the next step.

ii)—A solution of the compound (17.6 g) described under i in acetone (352 ml) was treated with a 6 M aqueous solution of hydrochloric acid (3.52 ml). After stirring of the reaction mixture for 3 h at 50° C., the mixture was concentrated under reduced pressure. The residue was poured into water and the product extracted into ethyl acetate. The combined organic phases were washed with water, dried over sodium sulfate, and concentrated under reduced pressure. Column chromatography afforded (3β,5α,20S)-4,4,20-trimethylpregna-6,8(14)-diene-3,21-diol 3-benzoate (7.69 g).

iii)—Following procedures analogous to those described under viii–xii of Example 1, the product of the previous step was converted to (3β,5α,20R)-4,4,20-trimethyl-21-phenylpregna-6,8(14)-dien-3-ol. M.p. 218–220° C.

EXAMPLE 4

(3β,5α,20S)-4,4,20-Trimethyl-21-(3-methylphenyl) pregna-8,14-diene-3,21-diol i)—Following a procedure analogous to that described under ix of Example 1, (3β,5α,20S)-3-(benzoyloxy)-4,4-dimethylpregna-8,14-diene-20-carboxaldehyde (compound 10; described in Example 1 under viii; 0.5 g) was converted to (3β,5α,20S)-4,4,20-trimethyl-21-(3-methylphenyl) pregna-8,14-diene-3,21-diol 3-benzoate (0.31 g).

ii)—Following a procedure analogous to that of step xii of Example 1, the product obtained in the previous step (0.31 g) was converted to (3β,5α,20S)-4,4,20-trimethyl-21-(3-methylphenyl)pregna-8,14-diene-3,21-diol (53 mg). M.p. 169–173° C.

EXAMPLE 5

(3β,5α,20R)-4,4-Dimethyl-23-(2-methylphenyl)-24-norchola-8,14-dien-3-ol i)—p-Toluenesulfonic anhydride (20 g) was added to an ice-cooled solution of (3β,5α,20S)-4,4,20-trimethylpregna-8,14-diene-3,21-diol 3-benzoate (compound 9; prepared as described under vii of Example 1; 10 g) in dry pyridine (40 ml). The reaction mixture was stirred overnight at room temperature and then poured into water (400 ml). After stirring of the mixture for 1 h, the resulting precipitate was collected by filtration and washed with water. Drying at 50° C. under reduced pressure gave (3β,5α,20S)-4,4,20-trimethyl-21-[[(4-methylphenyl)sulfonyl]oxy]-pregna-8,14-dien-3-ol benzoate (14.1 g), which was used in the following step without further purification.

ii)—A suspension of the tosylate (9.12 g) described under i in dry dimethyl sulfoxide (31 ml) was heated at 50° C. Potassium cyanide (3.86 g) was added and the mixture was stirred for 6 h. Dry dimethyl sulfoxide (31 ml) was added and stirring was continued for another 10 h. After cooling, the mixture was poured into ice-water (600 ml). The precipitate was collected by filtration and washed with water. Drying at 50° C. under reduced pressure gave (3β,5α,20R)-3-(benzoyloxy)-4,4,20-trimethylpregna-8,14-diene-21-carbonitrile (6.45 g), which was used in the following step without further purification.

iii)—Diisobutylaluminium hydride (64 ml of a 20% solution in toluene) was added to a solution of the nitrile (6.40 g) described under ii in dry toluene (64 ml). The mixture was stirred overnight at room temperature whereafter the reaction was quenched with a 4 M aqueous solution of hydrochloric acid (71 ml). After filtration, the product was extracted into ethyl acetate. The combined organic phases were washed with water, dried over sodium sulfate, and concentrated under reduced pressure to give (3β,5α,20R)-3-hydroxy-4,4,20-trimethylpregna-8,14-diene-21-carboxaldehyde (4.59 g), which was used in the following step without further purification.

iv)—Pyridinium p-toluenesulfonate (0.29 g) was added to a solution of the aldehyde (4.59 g) described under iii in dry dichloromethane (28 ml) and ethyl vinyl ether (9.1 ml). After stirring of the mixture for 1 h pyridine (1 ml) was added. The mixture was washed with water, dried over sodium sulfate, and concentrated under reduced pressure to give (3β,5α,20R)-3-[(1-ethoxyethyl)oxy]-4,4,20-trimethylpregna-8,14-diene-21-carboxaldehyde (5.64 g), which was used in the following step without further purification.

v)—Following a procedure analogous to that described under ix of Example 1, the carboxaldehyde obtained in the previous step (1.0 g) was converted to (3β,5α,20R)-3-[(1-ethoxyethyl)oxy]-4,4-dimethyl-23-(2-methylphenyl)-24-norchola-8,14-dien-23-ol (1.63 g).

vi)—Following a procedure analogous to that described under x of Example 1, the alcohol (1.60 g) obtained in the previous step was converted to (3β,5α,20R)-3-[(1-ethoxyethyl)oxy]-4,4-dimethyl-23-(2-methylphenyl)-24-norchola-8,14-dien-23-ol methyl ethanedioate (2.11 g).

vii)—Following a procedure analogous to that described under xi of Example 1, the methyl ethanedioate (2.11 g) obtained in the previous step was converted to (3β,5α,20R)-3-[(1-ethoxyethyl)oxy]-4,4-dimethyl-23-(2-methylphenyl)-24-norchola-8,14-diene (3.64 g).

viii)—A solution of the compound (3.64 g) described under vii in acetone (20 ml) was treated with a 4 M aqueous solution of hydrochloric acid (2 ml). After stirring of the reaction mixture for 1 h, the mixture was poured into water and the product extracted into ethyl acetate. The combined organic phases were washed with water, dried over sodium sulfate, and concentrated under reduced pressure. Crystallization from dichloromethane/acetone afforded (3β,5α,20R)-4,4-dimethyl-23-(2-methylphenyl)-24-norchola-8,14-dien-3-ol (0.40 g). M.p. 184–186° C.

EXAMPLE 6

Starting from (3β,5α,20R)-3-[(1-ethoxyethyl)oxy]-4,4,20-trimethylpregna-8,14-diene-21-carboxaldehyde, described under iv of Example 5, and using reaction steps analogous to those described under v–viii of Example 5, the following compounds were prepared:

A)—(3β,5α,20R)-4,4-Dimethyl-23-(3-methylphenyl)-24-norchola-8,14-dien-3-ol. M.p. 159–161° C.

B)—(3β,5α,20R)-4,4-Dimethyl-23-[2-(trifluoromethyl)phenyl]-24-norchola-8,14-dien-3-ol. M.p. 130–147° C. The product contained 45% of (3β,5α,20R)-4,4-dimethyl-23-[2-(trifluoromethyl)phenyl]-24-norchola-6,8(14)-dien-3-ol.

EXAMPLE 7

(3β,5α,20R)-4,4-Dimethyl-23-phenyl-24-norchola-8,14-dien-3-ol and (3β,5α,20R)-3-hydroxy-4,4-dimethyl-23-phenyl-24-norchola-8,14-dien-23-one i)—A mixture of (3β,20S)-21-[[(1,1-dimethylethyl)dimethylsilyl]oxy]-4,4,20-trimethylpregna-5,7-dien-3-ol benzoate (compound 8; Example 1, step vi; 46.5 g), chloroform (400 ml), and a solution of HCl in acetic acid (1 M, 400 ml) was stirred for 45 min. at room temperature and then heated under reflux for another 45 min. Another portion of the diene mentioned above (46.5 g) was treated in the same way. The reaction mixtures of both experiments were cooled, put together and concentrated under reduced pressure to remove the chloroform. The residue was poured into a solution of sodium hydroxide (150 g) in water (2.5 l). The resulting precipitate was collected by filtration, washed with water and dried. The crude product was crystallized from acetone to afford a 6:1 mixture (51.4 g) of (3β,5α,20S)-4,4,20-trimethylpregna-8,14-diene-3,21-diol 21-acetate 3-benzoate and (3β,5α,20S)-4,4,20-trimethylpregna-6,8(14)-diene-3,21-diol 21-acetate 3-benzoate. The mixture was used as such in the next step.

ii)—Potassium hydroxide (13.5 g) was added to a solution of the product obtained in the previous step (62 g) in tetrahydrofuran (400 ml), methanol (250 ml) and water (100 ml). The mixture was stirred for 1 h at room temperature and then poured into water (10 l). The resulting precipitate was collected by filtration, washed with water and dried to give (3β,5α,20S)-4,4,20-trimethylpregna-8,14-diene-3,21-diol 3-benzoate (58 g). The product was used in the following step without further purification.

iii)—Following procedures analogous to those described under i–iii of Example 5 the alcohol obtained in the previous step was converted to give (3β,5α,20R)-3-hydroxy-4,4,20-trimethylpregna-8,14-diene-21-carboxaldehyde.

iv)—A solution of the aldehyde (12.3 g) mentioned above in dry pyridine (150 ml) was cooled to 4° C. Benzoyl chloride (8 ml) was added in 5 min. and the reaction mixture was stirred for 1.5 h at room temperature. Then it was poured into water (2 l) and the resulting mixture was stirred overnight. The product was extracted into dichloromethane and the combined organic phases were concentrated under reduced pressure to give (3β,5α,20R)-3-(benzoyloxy)-4,4,20-trimethylpregna-8,14-diene-21-carboxaldehyde (16.1 g). The product was used in the following step without further purification.

v)—Following a procedure analogous to that described under ix of Example 1, the aldehyde obtained in the previous step (15.0 g) was converted to a mixture of 23R and 23S phenylcarbinols which could be separated by column chromatography to afford (3β,5α,20R,23R)-4,4-dimethyl-23-phenyl-24-norchola-8,14-diene-3,23-diol 3-benzoate (2.15 g) and (3β,5α,20R,23S)-4,4-dimethyl-23-phenyl-24-norchola-8,14-diene-3,23-diol 3-benzoate (2.95 g).

vi)—A suspension of Raney nickel in water (100 g) was added to a solution of (3β,5α,20R,23R)-4,4-dimethyl-23-phenyl-24-norchola-8,14-diene-3,23-diol 3-benzoate (1.95 g) in ethanol (150 ml) and the mixture was stirred at room temperature for 96 h. The Raney nickel was removed by filtration. In another experiment (3β,5α,20R,23S)-4,4-dimethyl-23-phenyl-24-norchola-8,14-diene-3,23-diol 3-benzoate (1.30 g) was treated in the same way. The filtrates of both experiments were put together and concentrated under reduced pressure. The crude product was purified by chromatography to afford (3β,5α,20R)-4,4-dimethyl-23-phenyl-24-norchola-8,14-dien-3-ol benzoate (1.00 g) and (3β,5α,20R)-3-(benzoyloxy)-4,4-dimethyl-23-phenyl-24-norchola-8,14-dien-23-one (0.40 g).

viiA)—Following a procedure analogous to that described under iv of Example 1 (3β,5α,20R)-4,4-dimethyl-23-phenyl-24-norchola-8,14-dien-3-ol benzoate (1.20 g) was converted to the 3-hydroxy compound to give, after crystallization from ethanol, (3β,5α,20R)-4,4-dimethyl-23-phenyl-24-norchola-8,14-dien-3-ol (0.65 g). M.p. 164.3–165.7° C.

viiB)—Sodium hydroxide (0.40 g) was added to a solution of (3β,5α,20R)-3-(benzoyloxy)-4,4-dimethyl-23-phenyl-24-norchola-8,14-dien-23-one (0.70 g) in tetrahydrofuran (10 ml), methanol (10 ml), dichloromethane (1 ml) and water (1 ml). The reaction mixture was heated at reflux temperature for 6 h, cooled, and neutralized with acetic acid (1 ml). The product was extracted into dichloromethane and the combined organic phases were concentrated under reduced pressure. Crystallization of the crude product from ethanol gave (3β,5α,20R)-3-hydroxy-4,4-dimethyl-23-phenyl-24-norchola-8,14-dien-23-one (0.30 g). M.p. 196.4–197.2° C.

EXAMPLE 8

(3β,5α,20R,23R)-4,4-Dimethyl-23-phenyl-24-norchola-8,14-diene-3,23-diol

Following a procedure analogous to that described under iv of Example 1 (3β,5α,20R,23R)-4,4-dimethyl-23-phenyl-24-norchola-8,14-diene-3,23-diol 3-benzoate (Example 7, step v; 0.75 g) was converted to the 3-hydroxy compound to give, after crystallization from ethanol, (3β,5α,20R,23R)-4,4-dimethyl-23-phenyl-24-norchola-8,14-diene-3,23-diol (0.28 g). M.p. 199.2–200.7° C.

EXAMPLE 9

(3β,5α,20R,23S)-4,4-Dimethyl-23-phenyl-24-norchola-8,14-diene-3,23-diol

Following a procedure analogous to that described under iv of Example 1 (3β,5α,20R,23S)-4,4-dimethyl-23-phenyl-24-norchola-8,14-diene-3,23-diol 3-benzoate (Example 7, step v; 0.75 g) was converted to the 3-hydroxy compound to give, after crystallization from ethanol, (3β,5α,20R,23S)-4,4-dimethyl-23-phenyl-24-norchola-8,14-diene-3,23-diol (0.13 g). M.p. 208.0–209.3° C.

EXAMPLE 10

(3β,5α,20R,22E)-4,4-Dimethyl-23-phenyl-24-norchola-8,14,22-trien-3-ol i)—Potassium t-butoxide (1.12 g) was added to a suspension of benzyltriphenylphosphonium chloride (4.22 g) in dry toluene (30 ml). The mixture was heated at 70° C. for 45 min. (3β,5α,20S)-3-(Benzoyloxy)-4,4-dimethylpregna-8,14-diene-20-carboxaldehyde (compound 10; Example 1, step viii; 1.0 g) was added and heating was continued for 1 h. After cooling, the mixture was poured into water and the product extracted into ethyl acetate. The combined organic phases were washed with water, dried over sodium sulfate, and concentrated under reduced pressure. Column chromatography afforded (3β,5α,20R,22E)-4,4-dimethyl-23-phenyl-24-norchola-8,14,22-trien-3-ol benzoate (0.70 g).

ii)—Following a procedure analogous to that of step xii of Example 1, the product obtained in the previous step (0.70 g) was converted to (3β,5α,20R,22E)-4,4-dimethyl-23-phenyl-24-norchola-8,14,22-trien-3-ol (0.23 g). M.p. 131–144° C. The product contained 30% of (3β,5α,20R,22E)-4,4-dimethyl-23-phenyl-24-norchola-6,8(14),22-trien-3-ol.

EXAMPLE 11

(3β,5α,20R,23E)-4,4-Dimethyl-24-phenylchola-8,14,23-trien-3-ol i)—Following a procedure analogous to that described under i of Example 10, (3β,5α,20R)-3-[(1-ethoxyethyl)oxy]-4,4,20-trimethylpregna-8,14-diene-21-carboxaldehyde (Example 5, step iv; 0.500 g) was converted to (3β,5α,20R,23E)-3-[(1-ethoxyethyl)oxy]-4,4-dimethyl-24-phenylchola-8,14,23-triene (0.86 g).

ii)—Following a procedure analogous to that described under viii of Example 5, the product obtained in the previous step (0.24 g) was converted to the 3-hydroxy compound. Column chromatography afforded (3β,5α,20R,23E)-4,4-dimethyl-24-phenylchola-8,14,23-trien-3-ol (0.139 g). M.p. 126.8–127.4° C. The compound contained 30% of (3β,5α,20R,23Z)-4,4-dimethyl-24-phenylchola-8,14,23-trien-3-ol.

EXAMPLE 12

(3β,5α,20S)-4,4-Dimethyl-23-phenyl-24-norchola-8,14-dien-22-yn-3-ol i)—Pyridinium chlorochromate (8.79 g) was added to a solution of (3β,5α,20S)-4,4,20-trimethylpregna-8,14-diene-3,21-diol 3-benzoate (Example 7, step ii; 12.6 g) in dry dichloromethane (130 ml). The reaction mixture was stirred at room temperature for 1.5 h. Another portion of pyridinium chlorochromate (1.50 g) was added and stirring was continued for another 1.5 h. The reaction mixture was filtered and the filtrate was poured into a saturated aqueous solution of sodium hydrogencarbonate. The product was extracted into dichloromethane and the combined organic phases were washed with water, dried over magnesium sulfate and concentrated under reduced pressure, to afford (3β,5α,20S)-3-(benzoyloxy)-4,4-dimethylpregna-8,14-diene-20-carboxaldehyde (10.3 g). The product was used in the following step without further purification.

ii)—A suspension of (chloromethyl)triphenylphosphonium chloride (17.5 g) in dry tetrahydrofuran (140 ml) was cooled to 0° C. Sodium t-butoxide (4.64 g) was added and the mixture was stirred for 20 min. A solution of the aldehyde obtained in the previous step (10.3 g) in dry tetrahydrofuran (80 ml) was added and the reaction mixture was stirred at 0° C. for 30 min. and at room temperature for another 2 h. Ethyl acetate was added and the mixture was concentrated to remove the tetrahydrofuran. Then it was washed with water and a mixture of a saturated aqueous solution of sodium hydrogencarbonate and brine. The organic phase was dried over magnesium sulfate and concentrated under reduced pressure. Column chromatography afforded (3β,5α,20S)-23-chloro-4,4-dimethyl-24-norchola-8,14,22-trien-3-ol benzoate (7.01 g).

iii)—Following a procedure analogous to that described under iv of Example 1, the product obtained in the previous step (7.01 g) was converted to (3β,5α,20S)-23-chloro-4,4-dimethyl-24-norchola-8,14,22-trien-3-ol (6.28 g).

iv)—Following a procedure analogous to that described under iv of Example 5, the product obtained in the previous step (6.28 g) was converted to (3β,5α,20S)-23-chloro-3-[(1-ethoxyethyl)oxy]-4,4-dimethyl-24-norchola-8,14,22-triene (6.98 g).

v)—A solution of the product of the previous step (6.98 g) in dry tetrahydrofuran (75 ml) was cooled to –20° C. n-Butyllithium in hexanes (1.6 M, 28.5 ml) was added in 20 min. and the reaction mixture was stirred at –20° C. for 15 min. and then at 0° C. for 3.5 h. Water was added and the product was extracted into ethyl acetate. The combined organic phases were washed with brine, dried over magnesium sulfate and concentrated under reduced pressure. Column chromatography afforded (3β,5α,20S)-3-[(1-ethoxyethyl)oxy]-4,4-dimethyl-24-norchola-8,14-dien-22-yne (4.34 g).

vi)—A mixture of the product of the previous step (0.50 g), iodobenzene (0.16 ml), palladium(II) acetate (16 mg), triphenylphosphine (62 mg) and copper(I) iodide (18 mg) in pyrrolidine (7 ml) was degassed and then heated at reflux temperature for 3 h. The reaction mixture was poured into a saturated aqueous solution of ammonium chloride and the product was extracted into ethyl acetate. The combined organic phases were washed with a saturated aqueous solution of ammonium chloride and brine and dried over magnesium sulfate. Column chromatography afforded (3β,5α,20S)-3-[(1-ethoxyethyl)oxy]-4,4-dimethyl-23-phenyl-24-norchola-8,14-dien-22-yne (0.62 g).

vii)—Following a procedure analogous to that described under viii of Example 5, the product obtained in the previous step (0.61 g) was converted to the 3-hydroxy compound. Column chromatography afforded (3β,5α,20S)-4,4-dimethyl-23-phenyl-24-norchola-8,14-dien-22-yn-3-ol (0.25 g). M.p. 136° C. The compound contained 20% of (3β,5α,20S)-4,4-dimethyl-23-phenyl-24-norchola-6,8(14)-dien-22-yn-3-ol.

EXAMPLE 13

Starting from (3β,5α,20S)-3-[(1-ethoxyethyl)oxy]-4,4-dimethyl-24-norchola-8,14-dien-22-yne, described under v of Example 12, and using reaction steps analogous to those described under vi and vii of that Example, the following compounds were prepared:

A)—(3β,5α,20S)-23-(4-Methoxyphenyl)-4,4-dimethyl-24-norchola-8,14-dien-22-yn-3-ol. M.p. 165.5° C. The product contained 30% of (3β,5α,20S)-23-(4-methoxyphenyl)-4,4-dimethyl-24-norchola-6,8(14)-dien-22-yn-3-ol.

B)—(3β,5α,20S)-23-(4-Chlorophenyl)-4,4-dimethyl-24-norchola-8,14-dien-22-yn-3-ol. The product contained 25% of (3β,5α,20S)-23-(4-chlorophenyl)-4,4-dimethyl-24-norchola-6,8(14)-dien-22-yn-3-ol.

EXAMPLE 14

(3β,5α,20R)-4,4-Dimethyl-24-phenylchola-8,14-dien-23-yn-3-ol i)—Following procedures analogous to those described under ii and v of Example 12, (3β,5α,20R)-3-[(1-ethoxyethyl)oxy]-4,4,20-trimethylpregna-8,14-diene-21-carboxaldehyde (Example 5, step iv) was converted to (3β,5α,20R)-3-[(1-ethoxyethyl)oxy]-4,4-dimethylchola-8,14-dien-23-yne.

ii)—Following procedures analogous to those described under vi and vii of Example 12, the alkyne described above was converted to (3β,5α,20R)-4,4-dimethyl-24-phenylchola-8,14-dien-23-yn-3-ol. M.p. 84.8–85.7° C. The product contained 15% of (3β,5α,20R)-4,4-dimethyl-24-phenylchola-6,8(14)-dien-23-yn-3-ol.

EXAMPLE 15

Starting from (3β,5α,20R)-3-[(1-ethoxyethyl)oxy]-4,4-dimethylchola-8,14-dien-23-yne, described under i of Example 14, and using reaction steps analogous to those described under vi and vii of Example 12, the following compounds were prepared:

A)—(3β,5α,20R)-24-(4-Methoxyphenyl)-4,4-dimethylchola-8,14-dien-23-yn-3-ol. M.p. 91.3–92.6° C. The product contained 15% of (3β,5α,20R)-24-(4-methoxyphenyl)-4,4-dimethylchola-6,8(14)-dien-23-yn-3-ol.

B)—(3β,5α,20R)-24-(4-Chlorophenyl-4,4-dimethylchola-8,14-dien-23-yn-3-ol. M.p. 128.2–129.4° C. The product contained 15% of (3β,5α,20R)-24-(4-chlorophenyl)-4,4-dimethylchola-6,8(14)-dien-23-yn-3-ol.

C)—(3β,5α,20R)-4,4-Dimethyl-24-(2-methylphenyl)chola-8,14-dien-23-yn-3-ol. M.p. 136.5–137.8° C.

D)—(3β,5α,20R)-4,4-Dimethyl-24-(4-methylphenyl)chola-8,14-dien-23-yn-3-ol. M.p. 111.2–112.1° C.

EXAMPLE 16

(3β,5α,20R)-20-Methyl-21-phenylpregna-8,14-dien-3-ol and (3β,5α,20R)-20-methyl-21-phenylpregna-6,8(14)-dien-3-ol i)—Following a procedure analogous to that described under v of Example 1, (3β,17Z)-pregna-5,17-dien-3-ol [82.7 g; see Drefahl, G. et al, Chem. Ber. 604 (1965)] was converted to (3β,17Z)-pregna-5,17-dien-3-ol benzoate (104.7 g).

ii)—A solution of the product (25.3 g) obtained in the previous step in dry dichloromethane (500 ml) was cooled to 15° C. Paraformaldehyde (11.3 g) was added, followed by boron trifluoride diethyl etherate (0.78 ml). The mixture was stirred for 45 min. and then filtered to remove the excess paraformaldehyde. Sulfuric acid (6 M, 31.3 ml) and methanol (250 ml) were added and the mixture was stirred at room temperature for 5 h. It was neutralized with an aqueous solution of sodium hydroxide (2 M) and then poured into water. The product was extracted into dichloromethane; the combined organic phases were dried over of sodium sulfate and concentrated under reduced pressure to give (3β,20S)-20-methylpregna-5,16-diene-3,21-diol 3-benzoate (26.5 g). The product was used in the following step without further purification.

iii)—A solution of the alcohol obtained in the previous step (13.3 g) in dichloromethane (135 ml) and ethanol (135 ml), containing platinum on activated carbon (10%, 4.18 g), was hydrogenated at room temperature and atmospheric pressure. The solution was filtered and concentrated under reduced pressure. Crystallization from dichloromethane/acetone afforded (3β,20S)-20-methylpregn-5-ene-3,21-diol 3-benzoate (10.6 g).

iv)—A solution of the alcohol obtained in the previous step (22.2 g) in dry dichloromethane (444 ml) was added to a suspension of pyridinium chlorochromate (44.3 g) in the same solvent (443 ml). After 2.5 h stirring at room temperature the reaction mixture was cooled to 5° C. An aqueous solution of sodium bisulfite (90 g) in water (511 ml) was added and stirring was continued for 1 h. The mixture was poured into water (3 l) and filtered over a mixture of silica and celite. The product was extracted into dichloromethane and the combined organic phases were concentrated under reduced pressure. The residu was dissolved in a mixture of ethyl acetate and tetrahydrofuran and washed with water. The organic phase was dried over sodium sulfate and treated with activated carbon, filtered, and concentrated to give (3β,20S)-3-(benzoyloxy)pregn-5-ene-20-carboxaldehyde (19.0 g). The product was used in the following step without further purification.

v)—Following a procedure analogous to that described under ix of Example 1, the aldehyde obtained in the previous step (19.0 g) was converted to a mixture of (3β,20S,21R)-20-methyl-21-phenylpregn-5-ene-3,21-diol 3-benzoate and (3β,20S,21S)-20-methyl-21-phenylpregn-5-ene-3,21-diol 3-benzoate (together 17.7 g).

vi)—A solution of the mixture of alcohols obtained in the previous step (15.3 g) and triethylsilane (5.26 ml) in dry dichloromethane (306 ml) was cooled to 0° C. Boron trifluoride diethyl etherate (4.2 ml) was added and the mixture was stirred for 1.5 h. The mixture was poured into a saturated aqueous solution of sodium hydrogencarbonate and the product was extracted into dichloromethane. The combined organic phases were washed with brine, dried over sodium sulfate and concentrated under reduced pressure. Crystallization of the crude product from diethyl ether afforded (3β,20R)-20-methyl-21-phenylpregn-5-en-3-ol benzoate (10.7 g).

vii)—A solution of the benzoate obtained in the previous step (8.88 g) in dry cyclohexane (450 ml) containing 1,3-dibromo-5,5-dimethylhydantoin (3.78 g) was heated under reflux for 1 h. The reaction mixture was cooled and poured into water. The product was extracted into ethyl acetate and the combined organic phases were washed with brine, dried over sodium sulfate and concentrated under reduced pressure. The residue (11.3 g) was dissolved in dry tetrahydrofuran (180 ml) and treated with a solution of tetrabutylammonium fluoride in tetrahydrofuran (1 M, 52.8 ml). The mixture was stirred overnight at room temperature. Then it was poured into water and the product was extracted into ethyl acetate. The combined organic phases were washed with brine, dried over sodium sulfate and concentrated under reduced pressure. Crystallization and column chromatography of the crude product afforded (3β,20R)-20-methyl-21-phenylpregna-5,7-dien-3-ol benzoate (4.48 g).

viii)—Following a procedure analogous to that described under vii of Example 1, the diene obtained in the previous step (3.2 g) was isomerized. Repeated crystallization of the crude product (3.3 g) from acetoneldiethyl ether and chromatography afforded (3β,5α,20R)-20-methyl-21-phenylpregna-8,14-dien-3-ol benzoate (1.51 g) and (3β,5α,20R)-20-methyl-21-phenylpregna-6,8(14)-dien-3-ol benzoate (0.75 g).

ixA)—Following a procedure analogous to that described under iv of Example 1, (3β,5α,20R)-20-methyl-21-phenylpregna-8,14-dien-3-ol benzoate (0.90 g) was converted to the 3-hydroxy compound. Repeated crystallization from diethyl ether/heptane gave (3β,5α,20R)-20-methyl-21-phenylpregna-8,14-dien-3-ol (0.39 g). M.p. 156–157° C.

ixB)—Following a procedure analogous to that described under iv of Example 1, (3β,5α,20R)-20-methyl-21-phenylpregna-6,8(14)-dien-3-ol benzoate (0.75 g) was converted to the 3-hydroxy compound. Chromatography and freeze-drying from dioxane/t-butanol gave (3β,5α,20R)-20-methyl-21-phenylpregna-6,8(14)-dien-3-ol (0.21 g).

EXAMPLE 17

(3β,5α,20R)-4,4-Dimethyl-23-(2-methylphenyl)-24-norchola-8,14-dien-3-ol hydrogen butanedioate A mixture of (3β,5α,20R)-4,4-dimethyl-23-(2-methylphenyl)-24-norchola-8,14-dien-3-ol (0.15 g), described under Example 5, dry pyridine (2.2 ml), succinic anhydride (0.82 g), and 4-dimethylaminopyridine (5 mg) was heated overnight at 60° C. The reaction mixture was cooled and subsequently poured into water and the product extracted into ethyl acetate. The combined organic phases were washed with a 2 M aqueous solution of hydrochloric acid and with water, dried over sodium sulfate, and concentrated under reduced pressure. Crystallization of the crude material from acetone afforded (3β,5α,20R)-4,4-dimethyl-23-(2-methylphenyl)-24-norchola-8,14-dien-3-ol hydrogen butanedioate (0.106 g). M.p. 144–147° C.

EXAMPLE 18

In a manner analogous to that described in Example 17, the following compounds were prepared:

A)—(3β,5α,20R)-4,4,20-Trimethyl-21-phenylpregna-8,14-dien-3-ol hydrogen butanedioate from (3β,5α,20R)-4,4,20-trimethyl-21-phenylpregna-8,14-dien-3-ol (compound 1, described in Example 1). The product contained 30% of (3β,5α,20R)-4,4,20-trimethyl-21-phenylpregna-6,8(14)-dien-3-ol hydrogen butanedioate.

B)—(3β,5α,20R)-4,4,20-Trimethyl-21-[4-(trifluoromethyl)phenyl]pregna-8,14-dien-3-ol hydrogen butanedioate from (3β,5α,20R)-4,4,20-trimethyl-21-[4-(trifluoromethyl)phenyl]pregna-8,14-dien-3-ol (described in Example 2B). M.p. 147–151° C.

C)—(3β,5α,20R)-4,4-Dimethyl-23-[2-(trifluoromethyl)phenyl]-24-norchola-8,14-dien-3-ol hydrogen butanedioate from (3β,5α,20R)-4,4-dimethyl-23-[2-(trifluoromethyl)phenyl]-24-norchola-8,14-dien-3-ol (described in Example 6B). The product contained 30% of (3β,5α,20R)-4,4-dimethyl-23-[2-(trifluoromethyl)phenyl]-24-norchola-6,8(14)-dien-3-ol hydrogen butanedioate.

D)—(3β,5α,20R,22E)-4,4-Dimethyl-23-phenyl-24-norchola-8,14,22-trien-3-ol hydrogen butanedioate from (3β,5α,20R,22E)-4,4-dimethyl-23-phenyl-24-norchola-8,14,22-trien-3-ol (described in Example 10). The compound contained 40% of (3β,5α,20R,22E)-4,4-dimethyl-23-phenyl-24-norchola-6,8(14),22-trien-3-ol hydrogen butanedioate.

EXAMPLE 19

The Oocyte Assay

General:

Oocytes arrested in meiose contain diffused chromosomes which are surrounded by an intact nuclear envelope known as the germinal vesicle (GV). Upon reinitiation of meiosis by the midcycle gonadotropin surge, the chromosomes recondense and the GV breaks down (GVBD). In vivo, the oocyte is exposed to hypoxanthin (HX), which maintains the oocyte arrested in the meiotic prophase. This meiotic arrest can be mimicked in vitro by addition of hypoxanthin to the culture medium. The activity of the compounds of the invention is measured as the ability to overcome the hypoxanthin maintained meiotic arrest in denuded oocytes (DO), i.e. the induction of meiotic resumption in vitro.

Isolation of Cumulus Enclosed Oocytes:

Ovaries are obtained from immature female mice (B6D2-F1, strain C57BLxDBA). At the age of 19, 20 or 21 days the mice are injected subcutaneously with a single dose of 20 IU Humegon (Organon, The Netherlands) in saline.

Forty-eight hours after Humegon injection mice are killed by cervical dislocation. The ovaries are removed, freed of extraneous tissue and placed in a multidish containing 1 ml preparation medium at 37° C. L-15 Leibovitz medium (Gibco, pH 7.3±0.1) supplemented with bovine serum albumin (3 mg.ml$^{-1}$), L-glutamine (0.23 mM), sodium pyruvate (2 mM) and hypoxanthin (4 mM) is used as preparation medium. The antral follicles of the ovaries are punctured under a dissecting microscope using two 27-gauge needles attached to two 1 ml syringes. Cumulus enclosed oocytes (CEO) of uniform size are selected with a mouth-controlled pipette and rinsed in 0,5 ml fresh preparation medium. About 20 CEO are obtained from one ovary.

Isolation of Denuded Oocytes:

Oocytes freed from cumulus cells, i.e. denuded oocytes (DO) are obtained by gently flushing CEO through a fine-bore mouth-controlled pipette. DO are rinsed twice in fresh culture medium and stored in culture medium at 37° C. in 100% humidified atmosphere with 5% $CO_2$ in air.

Experimental Design:

The oocyte assay is performed in 3 blocks, each block represents the ovaries of one mouse (randomized block design). At t=0 DO of the first ovary of the first mouse, are spread over well 1 and 3 and oocytes of the second ovary over well 2 and 4 of a 4-well multidish containing 0.5 ml of culture medium to which a 20-aralkyl-5a-pregnane derivative of the invention is added (first block). Culture medium was used as control. The same procedure is performed for the second and third mouse (block 2 and 3). The culture medium used is MEM alpha medium (Gibco, pH 7.3±0.1) saturated with $CO_2$ and supplemented with bovine serum albumin (3 mg.ml$^{-1}$), L-glutamine (0.23 mM), sodium pyruvate (2 mM) and hypoxanthin (4 mM). In total, each control or test compound is tested on 30 oocytes (10 oocytes per block). At t=0 the number of DO with intact germinal vesicles (GV) or germinal vesicle break-down (GVBD) is counted under an inverted microscope with differential interference contrast equipment. Only oocytes with an intact GV are used in the experiment. Oocytes are cultured 22 hours at 37° C. in 100% humidified atmosphere with 5% $CO_2$ in air. At the end of the culture period the number of oocytes with GV or GVBD per group is counted. For statistical analysis the percentage germinal vesicle breakdown is calculated for each group in one block. These percentages are subjected to arcsin transformation, and differences between control and test compounds are analyzed by an ANOVA test for a randomized block design. Results are presented in Table I.

TABLE I

Percentage germinal vesicle breakdown (GVBD) in oocytes following culturing in the presence of test compounds (DO assay).*

| Compound (Example) | GVBD (%) Experiment (control) |
|---|---|
| (3β,5α,20R)-4,4,20-trimethyl-21-phenylpregna-8,14-dien-3-ol (1) | 100(0) |
| (3β,5α,20R)-4,4,20-trimethyl-21-(3-methylphenyl)pregna-8,14-dien-3-ol (2A) | 97(8) |
| (3β,5α,20R)-4,4,20-trimethyl-21-[4-(trifluoromethyl)phenyl]pregna-8,14-dien-3-ol (2B) | 98(0) |
| (3β,5α,20R)-4,4,20-trimethyl-21-phenylpregna-6,8(14)-dien-3-ol (3) | 100(0) |
| (3β,5α,20S)-4,4,20-trimethyl-21-(3-methylphenyl)pregna-8,14-diene,3,21-diol (4) | 19(4) |
| (3β,5α,20R)-4,4-dimethyl-23-(2-methylphenyl)-24-norchola-8,14-dien-3-ol (5) | 28(0) |
| (3β,5α,20R)-4,4-dimethyl-23-(3-methylphenyl)-24-norchola-8,14-dien-3-ol (6A) | 60(8) |
| (3β,5α,20R)-4,4-dimethyl-23-[2-(trifluoromethyl)phenyl]-24-norchola-8,14-dien-3-ol (6B) | 0(0) |
| (3β,5α,20R)-4,4-dimethyl-23-phenyl-24-norchola-8,14-dien-3-ol (7A) | |
| (3β,5α,20R)-3-hydroxy-4,4-dimethyl-23-phenyl-24-norchola-8,14-dien-23-one (7B) | |
| (3β,5α,20R,23R)-4,4-dimethyl-23-phenyl-24-norchola-8,14-diene-3,23-diol (8) | |
| (3β,5α,20R,23S)-4,4-dimethyl-23-phenyl-24-norchola-8,14-diene-3,23-diol (9) | |
| (3β,5α,20R,22E)-4,4-dimethyl-23-phenyl-24-norchola-8,14,22-trien-3-ol (10) | 0(0) |
| (3β,5α,20R,23E)-4,4-dimethyl-24-phenylchola-8,14,23-trien-3-ol (11) | 67(0) |
| (3β,5α,20S)-4,4-dimethyl-23-phenyl-24-norchola-8,14-dien-22-yn-3-ol (12) | 100(3) |
| (3β,5α,20S)-23-(4-methoxyphenyl)-4,4-dimethyl-24-norchola-8,14-dien-22-yn-3-ol (13A) | 5(0) |
| (3β,5α,20S)-23-(4-chlorophenyl)-4,4-dimethyl-24-norchola-8,14-dien-22-yn-3-ol (13B) | 60(0) |
| (3β,5α,20R)-4,4-dimethyl-24-phenylchola-8,14-dien-23-yn-3-ol (14) | 28(3) |
| (3β,5α,20R)-24-(4-methoxyphenyl)-4,4-dimethylchola-8,14-dien-23-yn-3-ol (15A) | 51(6) |
| (3β,5α,20R)-24-(4-chlorophenyl-)4,4-dimethylchola-8,14-dien-23-yn-3-ol (15B) | 39(6) |
| (3β,5α,20R)-4,4-dimethyl-24-(2-methylphenyl)chola-8,14-dien-23-yn-3-ol (15C) | 4(0) |
| (3β,5α,20R)-4,4-dimethyl-24-(4-methylphenyl)chola-8,14-dien-23-yn-3-ol (15D) | 100(0) |
| (3β,5α,20R)-20-methyl-21-phenylpregna-8,14-dien-3-ol (16A) | |
| (3β,5α,20R)-20-methyl-21-phenylpregna-6,8(14)-dien-3-ol (16B) | |
| (3β,5α,20R)-4,4-dimethyl-23-(2-methylphenyl)-24-norchola-8,14-dien-3-ol hydrogen butanedioate (17) | 81(0) |
| (3β,5α,20R)-4,4,20-trimethyl-21-phenylpregna-8,14-dien-3-ol hydrogen butanedioate (18A) | 38(6) |
| (3β,5α,20R)-4,4,20-trimethyl-21-[4-(trifluoromethyl)phenyl]pregna-8,14-dien-3-ol hydrogen butanedioate (18B) | 100(0) |
| (3β,5α,20R)-4,4-dimethyl-23-[2-(trifluoromethyl)phenyl]-24-norchola-8,14-dien-3-ol hydrogen butanedioate (18C) | 98(6) |
| (3β,5α,20R,22E)-4,4-dimethyl-23-phenyl-24-norchola-8,14,22-trien-3-ol hydrogen butanedioate (18D) | 100(6) |

TABLE I-continued

Percentage germinal vesicle breakdown (GVBD) in oocytes following culturing in the presence of test compounds (DO assay).*

| Compound (Example) | GVBD (%) Experiment (control) |
|---|---|
| (3β,5α,20R)-4,4-dimethylcholesta-8,14,24-trien-3-ol (FF-Mas) | 84(4) |

*Each compound was tested at a concentration of 10 μM.

What is claimed is:

1. A 20-aralkyl-5α-pregnane compound having the general formula I, or a pharmaceutically acceptable salt thereof,

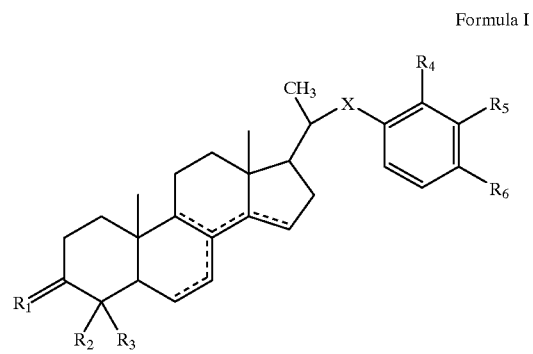

Formula I wherein $R_1$ is (H,OR), (H,OSO$_3$H) or NOR;

R is H, (C$_{1-6}$)alkyl or (C$_{1-6}$)acyl;

each of $R_2$ and $R_3$ is independently hydrogen or (C$_{1-6}$) alkyl;

X is a straight chain divalent C$_{1-8}$ hydrocarbon radical, optionally comprising a double or a triple bond; or X is —(CH$_2$)$_m$—CR$_7$R$_8$—; m=0–4;

at least one of $R_7$ and $R_8$ is (C$_{1-4}$)alkyl, hydroxy, (C$_{1-4}$) alkoxy or halogen; the other, if present, being hydrogen; or $R_7$ and $R_8$ together represent O or NOR';

R' is H, (C$_{1-6}$)alkyl or (C$_{1-6}$)acyl;

each of $R_4$, $R_5$ and $R_6$ is independently hydrogen, hydroxy, (C$_{1-4}$)alkoxy, halogen, NR$_9$R$_{10}$ or (C$_{1-4}$) alkyl, optionally substituted by hydroxy, alkoxy, halogen or oxo;

each of $R_9$ and $R_{10}$ is independently hydrogen or (C$_{1-4}$) alkyl; and the dotted lines indicate a $\Delta^7$ or a $\Delta^8$ double bond, or a pair of conjugated double bonds selected from $\Delta^{7,14}$, $\Delta^{8,14}$ and $\Delta^{6,8(14)}$;

provided that (3β,4α,24E)-25-(4-hydroxyphenyl)-4-methyl-26,27-dinorcholesta-7,24-dien-3-ol (gramisterol) is excluded.

2. A 20-aralkyl-5α-pregnane compound of claim 1, wherein $R_1$ is (H,OR) and the dotted lines indicate a pair of conjugated double bonds selected from $\Delta^{7,14}$, $\Delta^{8,14}$ and $\Delta^{6,8(14)}$.

3. A 20-aralkyl-5α-pregnane compound of claim 2, wherein the double bonds are $\Delta^{8,14}$.

4. A 20-aralkyl-5α-pregnane compound of claim 2, wherein the configuration of the 3-OR substituent is the β-configuration.

5. A 20-aralkyl-5α-pregnane compound of claim 1, wherein $R_1$ is (H,OR), R is H or $(C_{1-6})$acyl; each of $R_2$ and $R_3$ is independently hydrogen or $(C_{1-6})$alkyl; X is —$CH_2$—; $R_4$, $R_5$ and $R_6$ have the previously given meaning; the dotted lines indicate a pair of conjugated $\Delta^{8,14}$ double bonds; and wherein the configuration of the 3-OR substituent is the β-configuration.

6. A pharmaceutical composition comprising a 20-aralkyl-5α-pregnane compound having the general formula I, of claim 1 or a pharmaceutically acceptable salt thereof, in admixture with pharmaceutically acceptable auxiliaries.

7. A method of controlling fertility in a patient in need thereof, comprising administering to said patient an effective amount of a compound according to claim 1.

8. A process for preparing a pharmaceutical composition, comprising mixing together a compound of claim 1 with pharmaceutically acceptable auxiliaries.

* * * * *